United States Patent [19]
Ford et al.

[11] Patent Number: 5,639,466
[45] Date of Patent: Jun. 17, 1997

[54] METHOD FOR PACKAGING FOODSTUFFS

[75] Inventors: Thomas M. Ford, Greenville; William E. Kelly, Wilmington, both of Del.

[73] Assignee: Chronopol, Inc., Golder, Colo.

[21] Appl. No.: 393,775

[22] Filed: Feb. 24, 1995

Related U.S. Application Data

[63] Continuation-in-part of Ser. No. 201,496, Feb. 24, 1994, abandoned.

[51] Int. Cl.$^6$ ..................................................... A01N 25/08
[52] U.S. Cl. .......................... 424/412; 424/404; 424/414; 424/415; 424/485
[58] Field of Search .................................. 424/404, 408, 424/409, 410, 414, 415, 412; 514/557; 106/17, 18; 426/323, 326

[56] References Cited

U.S. PATENT DOCUMENTS

| | | | |
|---|---|---|---|
| 2,668,162 | 2/1954 | Lowe | 528/357 |
| 2,890,208 | 6/1959 | Young et al. | 528/357 |
| 2,906,646 | 9/1959 | Smith et al. | 117/144 |
| 3,636,956 | 1/1972 | Schneider | 128/335.5 |
| 3,645,941 | 2/1972 | Snapp et al. | 528/357 |
| 3,839,297 | 10/1974 | Wasserman et al. | 528/357 |
| 3,958,056 | 5/1976 | Brugh, Jr. et al. | 428/215 |
| 4,797,468 | 1/1989 | De Vries | 528/354 |
| 4,835,293 | 5/1989 | Bhatia | 549/274 |
| 5,023,349 | 6/1991 | Bhatia | 549/274 |
| 5,053,522 | 10/1991 | Muller | 549/274 |
| 5,143,720 | 9/1992 | Lopes | 424/55 |
| 5,180,765 | 1/1993 | Sinclair | 524/306 |
| 5,198,220 | 3/1993 | Damani | 424/426 |
| 5,208,297 | 5/1993 | Ford et al. | 525/415 |
| 5,223,546 | 6/1993 | Morita et al. | 521/52 |
| 5,338,822 | 8/1994 | Gruber et al. | 528/354 |
| B1 5,028,667 | 2/1993 | McClain et al. | 525/415 |

OTHER PUBLICATIONS

H.R. Kricheldorf and A. Seira, *Polymer Bullentin*, 14, 497–502, 1985.

J.W. Leinslag and A.J. Pennings, *Makromol Chem.*, 188, 1809–1814, 1987.

*Primary Examiner*—Neil S. Levy
*Attorney, Agent, or Firm*—Sheridan Ross P.C.

[57] ABSTRACT

An antibacterial composition and method for use of such composition in packaging of moisture-containing foodstuffs in a manner to extend the shelf life of the foods comprises placing the foodstuff in intimate contact with the composition which comprises 5–40% wt. of a lactic acid-based compound and optionally a liquid organic plasticizer dispersed in a solid matrix of poly(lactic acid) or lactic acid copolymer having a number average molecular weight of 3,000 to 200,000.

9 Claims, 7 Drawing Sheets

METHOD FOR PACKAGING FOODSTUFFS

CROSS REFERENCE TO RELATED APPLICATION

This application is a continuation-in-part of U.S. patent application Ser. No. 08/201,496, filed Feb. 24, 1994 now abandoned.

FIELD OF INVENTION

The invention relates to a composition and method for packaging moisture-containing foodstuffs. In particular, the invention relates to a method for packaging such foodstuffs in a manner to extend the shelf life of the food contained therein using a lactic acid-based compound as a source of lactic acid.

BACKGROUND OF THE INVENTION

Many moisture-containing food products such as meats are susceptible to oxidative flavor deterioration and microbial growth during storage, especially when the food is not frozen. Additives are often incorporated into the food or coated on the surface of the food to inhibit microbial growth and thus to enhance shelf life.

Lactic acid, because of its safety as an additive to food, is a material which has frequently been suggested as an agent to inhibit microbial growth. To this end lactic acid has been found to be effective to inhibit microbial growth on meat, including processed and low-fat meat products, poultry and seafood products. More particularly, lactic acid and salts thereof have been found to have substantial effect in inhibiting the growth of *E. coli, Listeria monocytogenes, Penicillin expansum, Saccharomyces cerevisiae, Pseudomonas fluorescens* and *Staphylococcus aureus*.

Though lactic acid and its derivatives have been extensively evaluated as antibacterial agents, their use has not heretofore been widespread. In part, this is because of the lack of a reliable and economical delivery system by which the lactic acid can be applied without the addition of substantial costs to the contained products.

SUMMARY OF THE INVENTION

Therefore, the invention is directed in its first aspect to an antibacterial composition, which is substantially free of water and lactic acid, comprising an homogeneous solid solution of:

a. 5–40% wt. lactic acid-based compound selected from the group consisting of lactide; liquid lactic acid oligomers, $(LA)_n$ wherein $n \geq 2$; and mixtures thereof;

b. 0–20% wt. organic liquid plasticizer which is recognized to be safe as an indirect additive to moisture-containing foodstuffs and has an atmospheric boiling point of at least 170° C.; and c. 60–95% wt. polymer having a number average molecular weight of 3,000–200,000 and selected from the group consisting of poly(lactic acid); copolymers of lactic acid containing at least 50 mole % lactic acid units; and mixtures thereof.

In a second aspect, the invention is directed to a packaging material suitable for extending the shelf life of moisture-containing foods in contact therewith comprising a polymeric substrate on which is coated a solid layer of the above-referred antibacterial composition having a thickness of at least 5 micrometers.

In a third aspect, the invention is directed to a method for extending the shelf life of moisture-containing foods by inhibiting the growth of bacteria thereon comprising applying a thin coating of water to the food, packaging the food in contact with the above-described antibacterial composition and maintaining the food in the package for a time sufficient to effect formation (by hydrolysis) and diffusion of the lactic acid into the moisture-containing food. Alternatively, the water coating can be applied to the contact side of the antibacterial composition.

BRIEF DESCRIPTION OF THE DRAWING

The Drawing consists of FIGS. 1–7 which are graphical representations showing the migration of lactic acid from polylactide films containing lactide under different conditions of extraction.

DETAILED DESCRIPTION OF THE INVENTION

General

The invention is directed broadly to a method for increasing the shelf life of moisture-containing foodstuffs, such as meats, by wrapping them in a film of poly(lactic acid) and lactide-containing composition which will supply lactic acid to the moist surface of the food, which increases the shelf life of the food by inhibiting bacterial growth thereon. The composition is comprised of a poly(lactic acid) polymer or copolymer, a lactic acid-based compound which is hydrolyzable to form lactic acid and, optionally, a minor amount of organic plasticizer to facilitate diffusion of the lactic acid or the lactic acid-based compound from the composition to the food interface.

Lactic Acid Polymer

Suitable polymers for use in the invention are poly(lactic acid) homopolymers and copolymers of lactic acid containing at least 50 mole % lactic acid units and mixtures thereof having a number average molecular weight ("Mn") of 3,000–200,000. It is preferred that the number average molecular weight of the polymer not exceed 100,000, lest the mobility of the lactide and/or oligomer be restricted too highly.

Poly(hydroxy acid)s such as poly(lactic acid) are typically prepared by the catalyzed ring-opening polymerization of the cyclic ester (lactone) or the dimeric cyclic ester of the monomer. Copolymers are typically prepared by catalyzed copolymerization of two or more cyclic esters and/or dimeric cyclic esters. Typical co-monomers are: glycolide (1,4-dioxane-2,5-dione), the dimeric cyclic ester of glycolic acid; the dimeric cyclic ester of lactic acid; β-propiolactone, the cyclic ester of 3-hydroxypropanic acid; α, α-dimethyl-β-propiolactone, the cyclic ester of 2,2-dimethyl-3-hydroxypropanic acid; β-butyrolactone, the cyclic ester of 3-hydroxybutyric acid; δ-valerolactone, the cyclic ester of 5-hydroxypentanoic acid; ε-caprolactone, the cyclic ester of 6-hydroxyhexanoic acid, and the lactones of its methyl substituted derivatives, such as 2-methyl-6-hydroxyhexanoic acid, 3-methyl-6-hydroxyhexanoic, 4-methyl-6-hydroxyhexanoic acid, 3,3,5-trimethyl-6-hydroxyhexanoic acid, etc.; dodecalactone, the cyclic ester of 2-(2-hydroxyethyl)-glycolic acid.

Because of its manner of preparation poly(lactic acid) is sometimes referred to as poly(lactide). As used herein, the terms "poly(lactic acid)" and "polylactide" are interchangeable.

Lactide is prepared by: (1) polymerizing lactic acid to form an oligomer, i.e., a relatively low molecular weight poly(lactic acid); (2) heating the oligomer, generally in the presence of a catalyst, to depolymerize it to lactide; and (3) recovering and purifying the lactide. See, for example, Lowe, U.S. Pat. No. 2,668,162; Bhatia, U.S. Pat. Nos. 4,835,293 and 5,023,349; DeVries, U.S. Pat. No. 4,797,468; and Muller, U.S. Pat. No. 5,053,522. Lactide may exist in any of four forms: D-, also known as D,D-; L-, also known as L,L-; D,L-; and meso.

Polymerization of cyclic esters and dimeric cyclic esters catalyzed by tin compounds is disclosed in Young, U.S. Pat. No. 2,890,208; Blood, U.S. Pat. No. 3,645,941; and Versfelt, U.S. Pat. No. 3,839,297. Tin compounds, such as stannous 2-ethylhexanoate (tin octoate) and other esters of tin (II) with carboxylic acids containing up to 18 carbon atoms as well as tetraphenyl tin, are well-known lactide polymerization catalysts. Polymerization with tin oxides is described in H. R. Kricheldorf and A. Serra, Polymer Bulletin, 14, 497–502, 1985. Polymerization of lactide with stannous 2-ethylhexanote is described in J. W. Leenslag and A. J. Pennings, Makromol. Chem. 188, 1809–1814 (1987). Typically about 0.01–1% by weight of tin catalyst is used.

Polymerization by yttrium compounds and by rare earth compounds has also been described. Polymerization of lactide with catalysts such as yttrium tris(methyl-S-lactate) and samarium tris(2-N,N-dimethylaminoethoxide) is described in McLain, U.S. Pat. No. 5,028,667. Polymerization of lactide with lanthanum bis(2,2,6,6-tetramethylheptane-3,5-dionato)-i-propoxide is described in Ford, U.S. Pat. No. 5,208,297.

Polymerization of lactide with ether complexes such as lanthanum tris(2,2,6,6-tetramethylheptanedionate) diethyleneglycoldiethyl ether complex is described in Ford, PCT Application PCT/US92/11309.

When copolymers of lactic acid are used in the invention, it is preferred that they contain at least 50 mole % lactic acid units. It is still further preferred that such copolymers contain at least 70 mole % lactic acid units.

Particularly preferred are star shaped block copolymers of PLA and poly(caprolactone), as described in U.S. patent application Ser. No. 230,994, filed Apr. 21, 1994, incorporated herein in its entirety by reference.

If the composition of the invention is to be applied as a self-supported film without a substrate, it is preferred that the number average molecular weight of the polymer (determined by gel permeation chromatography) be at least 25,000. On the other hand, when the composition is applied to a substrate, such as paperboard, polyester or poly (vinylidine chloride), the coating may have a molecular weight as low as 3,000.

In making packaging materials according to the invention in which the composition is applied to a substrate, it is preferred to use polymeric materials which are either oxygen resistant or moisture resistant and preferably resistant to both. Suitable substrates include coated paperboard, polyester, poly(vinylidene chloride), ethylene-vinyl alcohol copolymer and the like. Polyolefins can be used as a substrate for the compositions of the invention, but they do not exclude oxygen well.

Lactic Acid-based Compound

Lactic acid-based compounds which are suitable for use in the invention must be hydrolyzable to form liquid lactic acid which is capable of diffusion through the polymer matrix onto the surface of the moisture-containing food, e.g., fresh meat. In particular, suitable compounds are lactide and low molecular weight oligomers of lactic acid, i.e., oligomers in which the average number of monomeric units(n) is at least 2.

As discussed hereinabove, such oligomers are usually prepared by the dehydration of lactic acid and lactide is usually prepared by thermal cracking oligomers to form the corresponding cyclic diester (lactide). For this reason, it will preferred to employ oligomers in which n is even higher than 2 since they will thereby contain less water.

It is preferred to use lactide as the hydrolyzable component of the packaging material since that material is more readily hydrolyzable and is therefore more effective at a given concentration level. Nonetheless, low molecular weight lactic acid oligomers and mixtures thereof with lactic acid can be used with appropriate compositional changes.

Plasticizer

Suitable plasticizers for use in the invention are those which are liquid at normal temperatures, have an atmospheric boiling point of at least 170° C., and are approved for use as indirect food additives to moisture-containing foodstuffs. Such materials include plasticizers listed by the U.S. Food and Drug Administration in 21 CFR §§ 175.300 and 181.27, and include the following: acetyl tributyl citrate, acetyl triethyl citrate, p-tert-butylphenyl salicylate, butyl stearate, butylphthalyl butyl glycolate, dibutyl sebacate, di-(2-ethylhexyl) phthalate, diethyl phthalate, diisobutyl adipate, diisooctyl phthalate, diphenyl-2-ethylhexyl phosphate, epoxidized soybean oil, epoxidized linseed oil, ethylphthalyl ethyl glycolate, glycerol, glyceryl monooleate, glyceryl triacetate monoisopropyl citrate, mono-, di- and tri-stearyl citrate, propylene glycol, sorbitol, triacetin (glycerol triacetate), triethyl citrate and triethylene glycol.

The particular plasticizer selected for use in the invention will depend upon the specific composition of the material being prepared and its intended use. Some plasticizers, for example triethyl citrate, may act as a food source for bacteria and thus decrease the antimicrobial properties of the composition. Such plasticizers, while suitable in some applications; e.g. as coatings for polymeric substrates, might not be suitable for others; e.g. wrapping for fresh meat. Alternatively, the antibacterial activity of compositions containing such plasticizers may be maintained by increasing the amount of lactic acid-based component of the composition.

The optional plasticizer may be used in amounts of from about 5% wt. to about 20% wt. At amounts greater than about 20% wt., the physical properties of the film begin to be impaired. If used, it is preferred that the plasticizer be present in an amount from 8 to 15% by weight for optimum results. It will be recognized, however, that the optimum amount may vary widely depending upon the physical properties of the lactide polymer, lactic acid-based compound and plasticizer.

Since the plasticizer must be intimately dispersed within the polymer, it should not crystallize in the presence of the polymer at room temperature. Nevertheless, in order to prevent excessive evaporative losses during polymer processing, it is preferred that the atmospheric boiling point of the plasticizer exceed about 170° C. and, more preferably, 200° C. or higher. The decomposition temperature of the plasticizer must, of course, be higher than the highest processing temperature for the polymer.

Formulation

The compositions of the invention are easily made by melting the polymer and mixing in the optional liquid plasticizer and the hydrolyzable lactic acid-based compound under anhydrous conditions. It is essential that the composition and components be substantially dry since any water present will cause premature hydrolysis of the lactic acid precursor (lactide) and may cause hydrolysis of the lactic acid polymer as well. The components are substantially soluble and therefore are easily blended homogeneously with low energy input.

It is recognized that poly(lactic acid) upon standing in ambient air may absorb water from the air, which in turn can result in hydrolysis of the lactide or the polymer to form lactic acid. It is therefore preferred to prevent premature hydrolysis of the lactide. For this reason, the composition should contain no more than 1% by weight of either water or lactic acid. It is still further preferred that the composition contain no more 0.01% water and no more than 0.1% lactic acid.

Application

The above-described antibacterial composition is solid at room temperature, but can be applied to the food product to be protected by a variety of techniques. It can be formed as a self-supporting film for wrapping the food. It can also be coated on an appropriate polymeric substrate such as paperboard, polyester or polyolefin, which can then be used as a wrapper or formed as a container for the food.

Regardless of which application technique is used, it is preferred that the layer of composition in contact with the food be at least 5 micrometers (0.2 mil) in thickness and preferably 10 micrometers (0.4 mil) or more. The coating thickness will normally be adjusted to reflect the physical characteristics of the components and the diffusability of the lactic acid-based compound from the formulated coating to the food surface. Though thicker layers can be used, little advantage is obtained if film thickness exceeds about 50 micrometers (2 mils).

To facilitate the diffusive action of the lactide or oligomer, it is preferred that the moisture-containing food be coated with a thin layer of water before applying a film coating or placing the food in a container of the invention composition. Alternatively, the same end can be accomplished by applying a thin coating of water on the film before it is applied to the food or before the food is placed in a container of the invention composition.

EXAMPLES

Examples 1–4

A series of four tests was carried out in which the effectiveness of the invention compositions to provide a source of lactic acid was determined by subjecting various polylactide compositions to leaching by exposure to an aqueous solution of monobasic potassium phosphate. In particular, 0.6 g of each set of samples was cut into small pieces and placed into 6 mL of 0.2M monobasic potassium phosphate solution contained in small capped glass vials. The pH of each solution was adjusted with 2N NaOH. Samples of the liquid containing the leachate from each sample were taken at one-week time intervals over a period of seven weeks and the amount of lactic acid therein was measured by reversed phase High Performance Liquid Chromatography. These data were plotted as a function of time and are presented in FIGS. 1–7 hereto.

The composition and test conditions of tested materials are given in Tables 1 and 2 below, respectively.

TABLE 1

Composition of Extraction Test Materials

| Material No. | Polymer % wt. | Polymer Mol. Wt. | Plasticize % wt. | Lactide % wt. |
|---|---|---|---|---|
| X | 87 | 10,000 | None | 13 |
| Y | 77 | 44,000 | 10 | 13 |
| Z | 77 | 20,000 | 10 | 13 |

TABLE 2

Extraction Test Conditions

| Example No. | pH | Temperature (°F.) |
|---|---|---|
| 1 | 5.3 | 35 |
| 2 | 6.5 | 35 |
| 3 | 5.3 | 50 |
| 4 | 6.5 | 50 |

Figure 1:
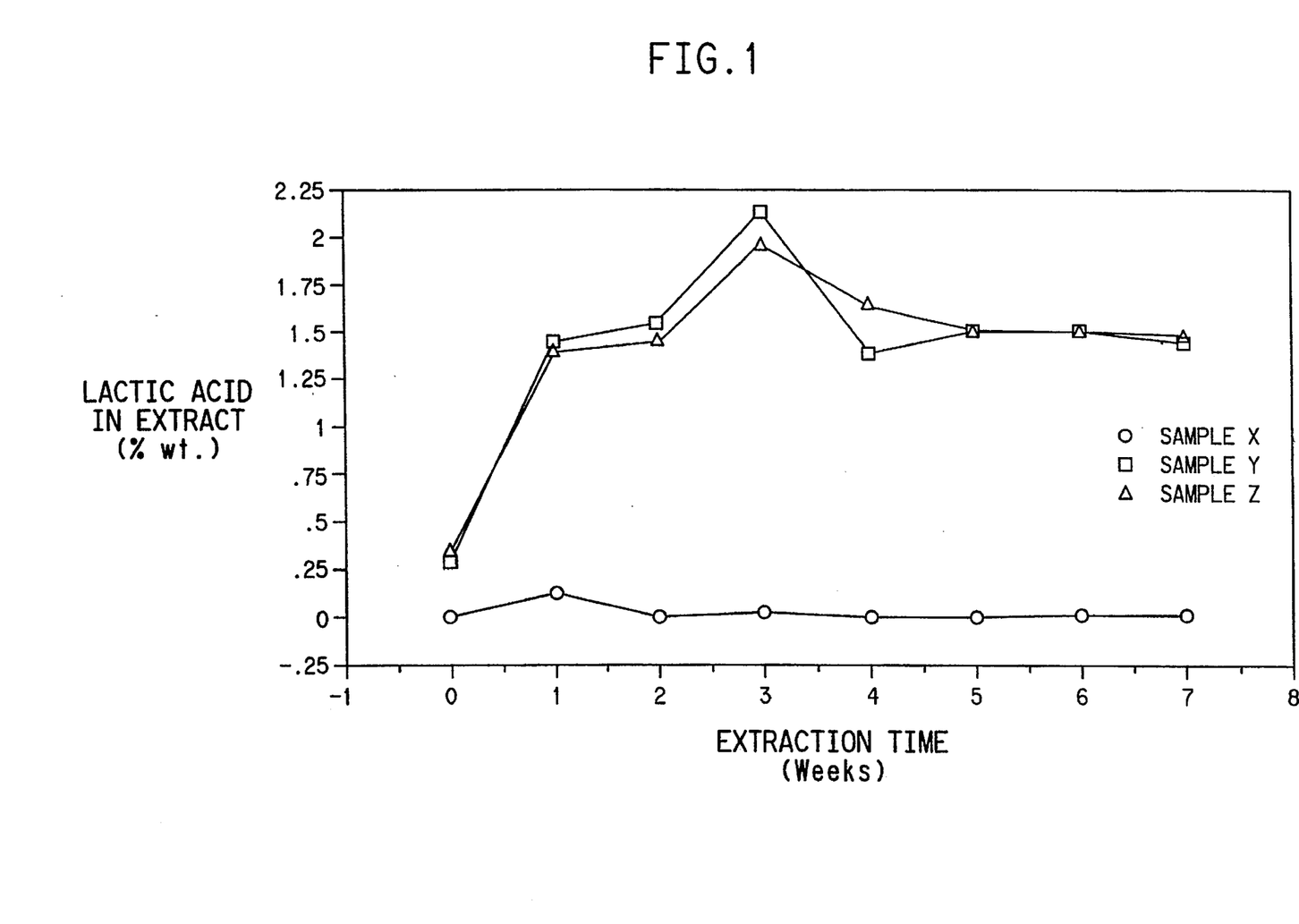

FIG. 1 shows that the plasticizer-free PLA/lactide composition (X) yielded almost no lactic acid under the conditions of Example 1. On the other hand, the plasticizer-containing compositions (Y and Z) exhibited substantial leaching of lactic acid throughout the seven week test period.

Figure 2:
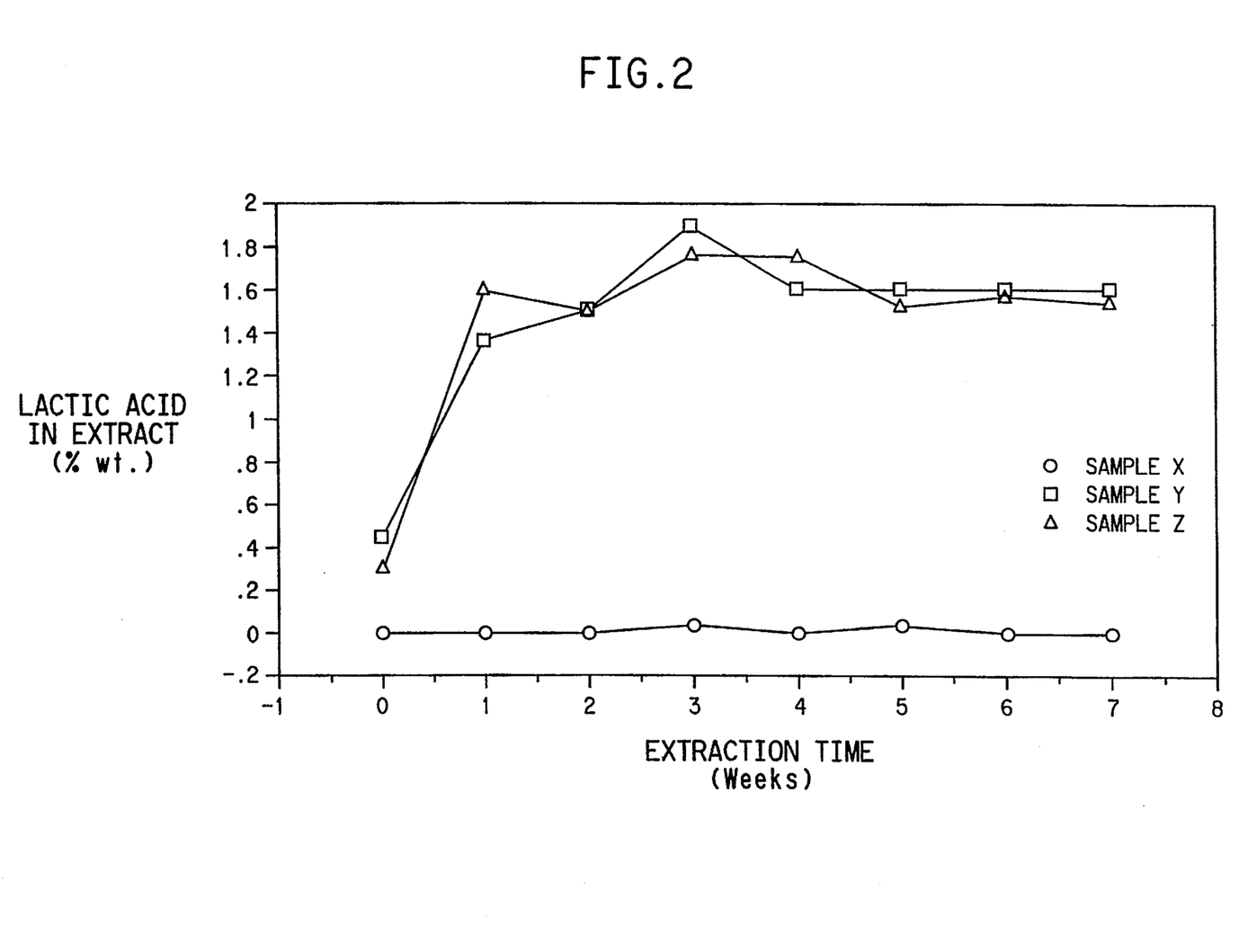

Similarly, FIG. 2 shows that the plasticizer-free composition (X) yielded almost no lactic acid under the higher pH conditions of Example 2. Again, the plasticizer-containing compositions (Y and Z) exhibited substantial leaching throughout the seven week test period.

Figure 3:
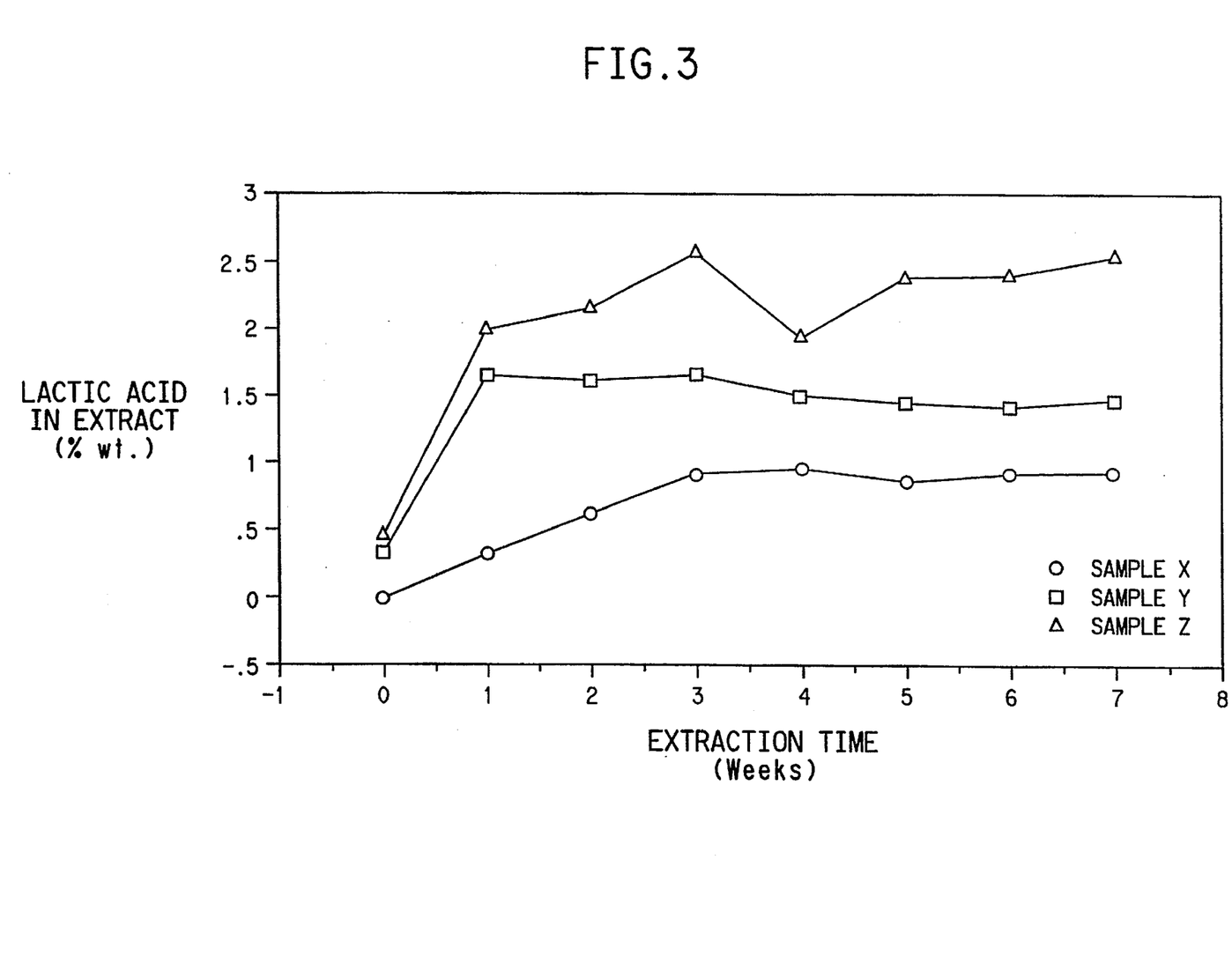
Figure 4:
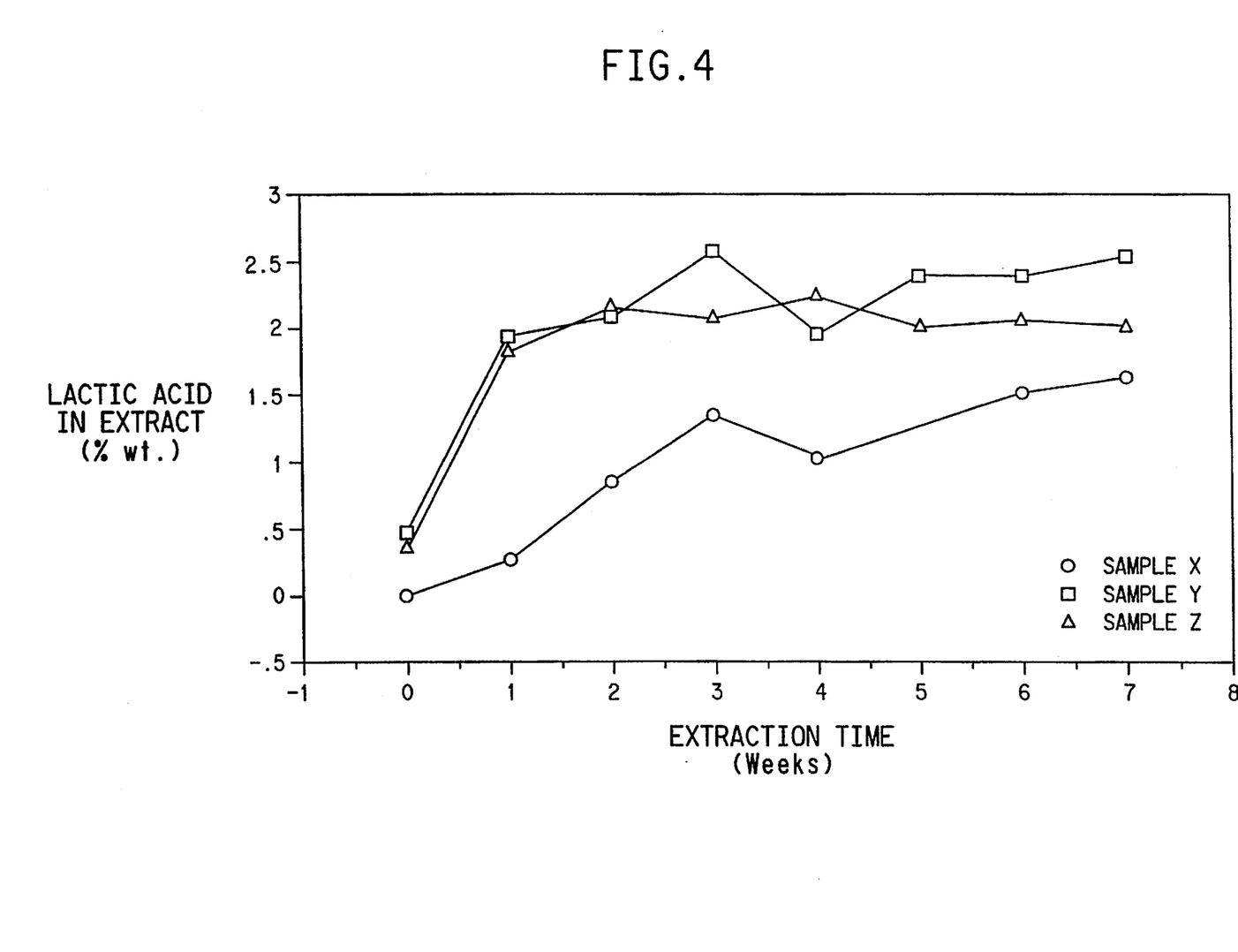

However, at the higher temperature conditions of Examples 3 and 4, it is shown by FIGS. 3 and 4 that some leaching of lactic acid takes place from the plasticizer-free material (X). However, the amount is significantly less than from those materials which contained plasticizer (Y and Z).

Figure 5:
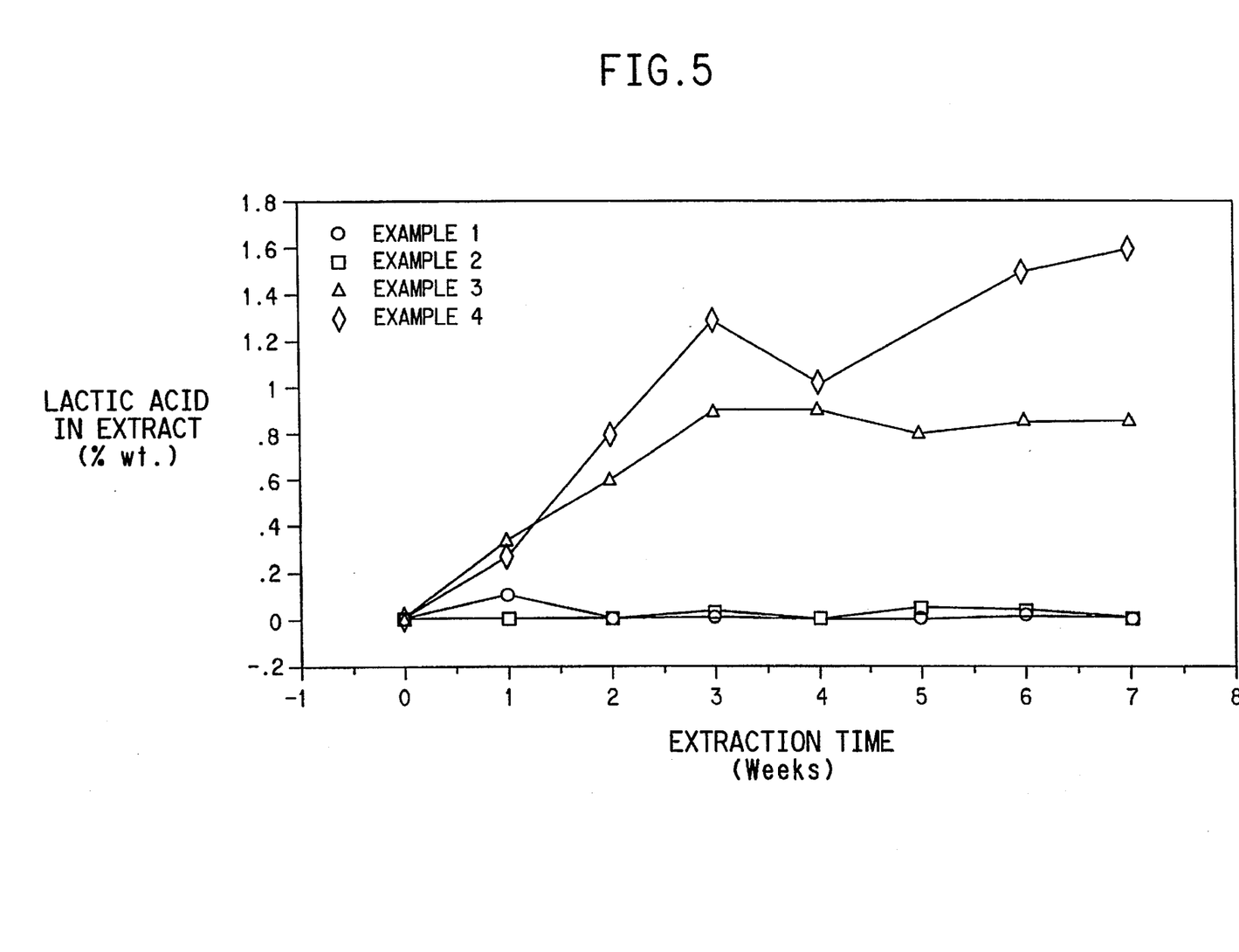

FIG. 5 shows graphically the negligible extraction of lactic acid from the plasticizer-free composition (X) under the conditions of both Examples 1 and 2. On the other hand, significant extraction takes place under the higher temperature conditions of Examples 3 and 4.

Figure 6:
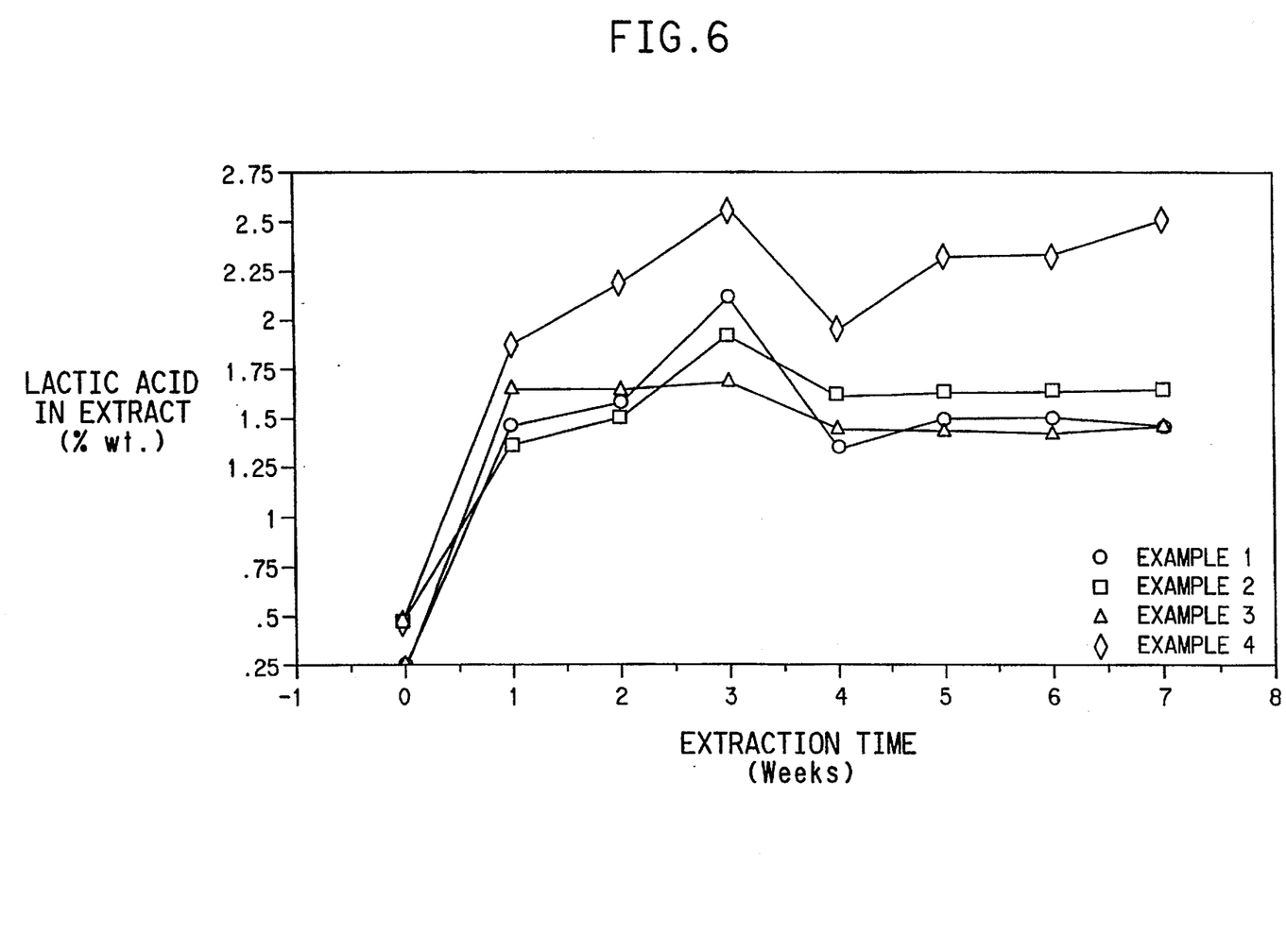
Figure 7:
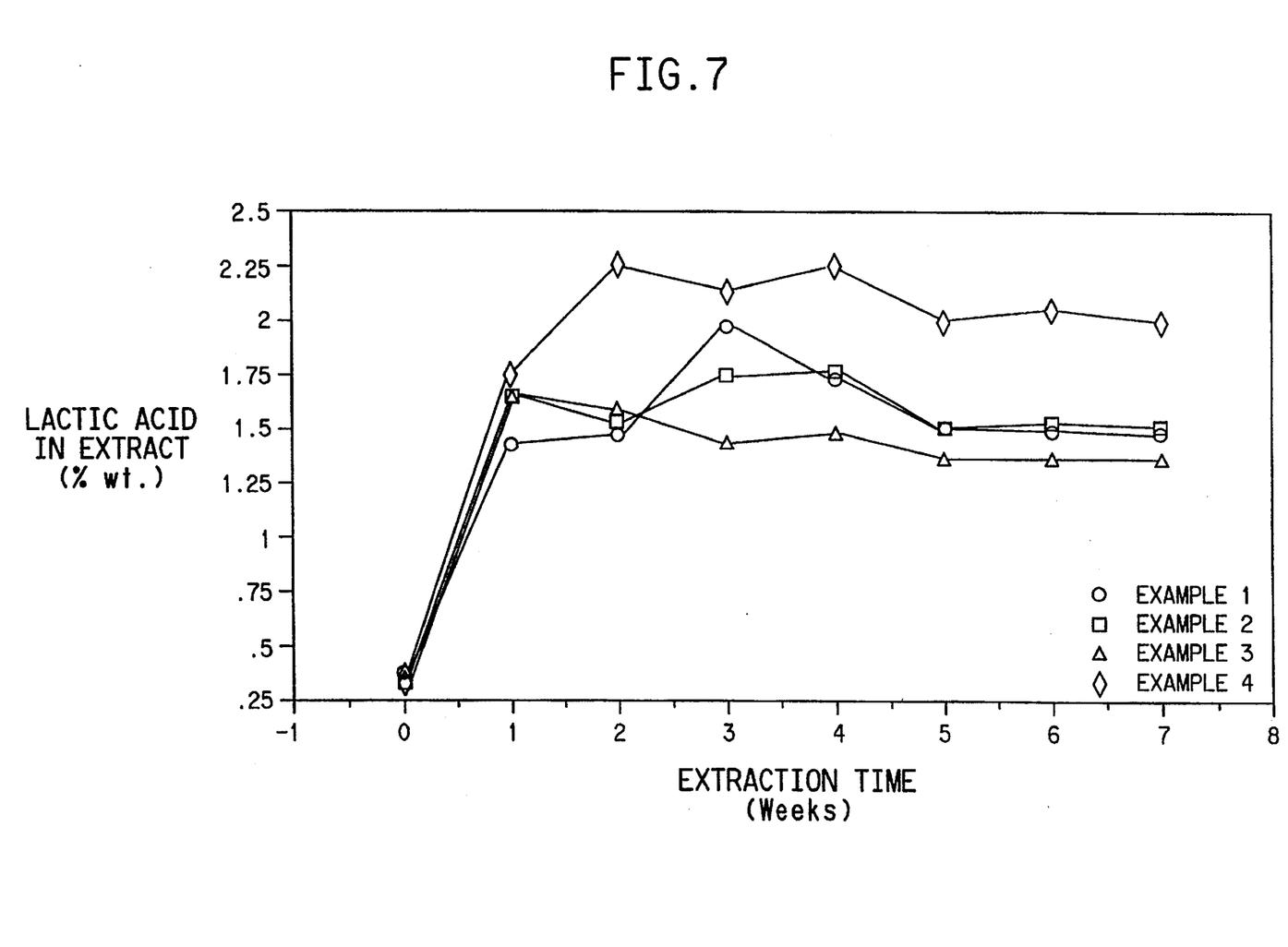

FIGS. 6 and 7 show that the plasticizer-containing compositions were effective with respect to lactic acid release under all the test conditions (Examples 1 through 4).

In summary, these data show that very little formation and migration of lactic acid is obtained if the polymer/lactide composition contains no additional plasticizer. On the other hand, very substantial formation and migration of lactic acid into the surrounding liquid is obtained if plasticizer is present. In all cases, higher temperature and pH yielded higher amounts of lactic acid in the surrounding liquid. Moreover, it was shown that at all pH and temperature levels, the use of higher molecular weight polymer (40,000 v. 20,000) gave higher yields of lactic acid in the surrounding liquid.

Examples 5–11

PLA samples in the form of fibers, tow and film were subjected to a Shake Flask Test in dilute phosphate buffer (pH=7.0) using the bacterium *Klebsiellia pneumoniae* (ATCC No. 4352) and Trypticase® Soy Agar plates. Inoculated and uninoculated agar plates served as controls, as well as Dacron® (E.I. du Pont de Nemours & Co.) with and without antimicrobial agent. The density of the bacteria was then measured at 1 hr., 24 hr., 7 days and 14 days after inoculation. Results are reported in Table 3.

TABLE 3

| Example No. | Example Type | Bacterial Density (CFU × 10⁴/ml.)[a] | | | | |
|---|---|---|---|---|---|---|
| | | Start | 1 hr. | 24 hr. | 7 dy | 14 dy |
| 5 | UC[b] | 0 | 0 | 0 | 0 | 0 |
| 6 | IC[c] | 8.95 | 9.58 | 18.0 | 31.1 | 21.5 |
| 7 | D[d] | 8.95 | 11.2 | 14.5 | 9.94 | 7.10 |
| 8 | D+[e] | 8.95 | 0 | 0 | 0 | 0 |
| 9 | Fiber[f] | 8.95 | 0 | 0 | 0 | 0 |
| 10 | Film[g] | 8.95 | 4.68 | 26.0 | 30.7 | 23.5 |
| 11 | Tow[g] | 8.95 | .125 | 0 | 0 | 0 |

Notes:
[a]Colony Forming Units.
[b]Uninoculated Control.
[c]Inoculated Control.
[d]Dacron ® without antimicrobial agent.
[e]Dacron ® with antimicrobial agent.
[f]Neat L-PLA with 0.25% wt. boric acid stabilizer.
[g]Neat L-PLA vdth 0.25% wt. boric acid and 7% wt. triethyl citrate
[h]A collection of approx. 100 fibers drawn and sized.

Examples 12–25

A series of PLA films were prepared and subjected to a Shake Flask Test as above, with the exception that measurements were not taken past 24 hours post inoculation. The composition of the films is set forth in Table 4. Test results are reported in Table 5.

TABLE 4

| Sample Film Designation | Added PLA (wt. %) | Measured PLA (pph)[1] | Added L-lactide (wt. %) | Measured L-lactide (pph)[1] |
|---|---|---|---|---|
| A | 100 | 96.4 | — | 3.6 |
| B | 90 | 90.8 | 10 | 9.2 |
| C | 85 | 85.4 | 15 | 14.6 |
| D | 75 | 81.0 | 25 | 19.0 |
| E | 70 | 72.0 | 30 | 28.0 |
| F | 65 | 65.3 | 35 | 34.7 |
| G | 60 | 62.7 | 40 | 37.3 |

Notes:
[1]Measured values determined by NMR and reported in parts per hundred (pph)

TABLE 5

| Example No. | Example Type | Bacterial Density (CFU × 10⁴/ml.) | | |
|---|---|---|---|---|
| | | Start | 1 hr. | 24 hr. |
| 12 | UC | 0 | 0 | 0 |
| 13 | IC | 11.1 | 12.6 | 20.9 |
| 14 | D | 11.1 | 13.6 | 21.2 |
| 15 | D+ | 11.1 | 0 | 0 |
| 16 | A | 11.1 | 11.0 | 16.2 |
| 17 | B | 11.1 | 10.9 | 19.3 |
| 18 | C | 11.1 | 9.7 | 19.9 |
| 19 | D | 11.1 | 8.35 | 23.6 |
| 20 | E | 11.1 | 3.95 | 0 |
| 21 | F | 11.1 | .105 | 0 |
| 22 | G | 11.1 | .175 | 0 |

What is claimed is:

1. A method for extending the shelf life of moisture-containing foods by inhibiting the growth of bacteria on the foods, comprising;

packaging the food in contact with an antibacterial composition which is a homogenous solid solution including (a) about 5–40% by weight of a lactic acid-based compound selected from the group consisting of lactide, lactic acid oligomer in which n=2–10 and mixtures thereof, (b) about 0–2% by weight organic liquid plasticizer which is recognized by the U.S. Food and Drug Administration to be safe as an indirect additive to moisture-containing foodstuffs and (c) about 60–95% by weight solid polymer having a number average molecular weight of about 3,000–200,000 and selected from the group consisting of poly(lactic acid), copolymers of lactic acid containing at least about 50 mole % lactic acid units, and mixtures thereof, and maintaining the food in the package for a time sufficient to produce an antimicrobial effect in the food.

2. A method, as claimed in claim 1, wherein said food is meat.

3. A method, as claimed in claim 1, wherein said step of packaging comprises wrapping said food in a film comprising polylactic acid.

4. A method, as claimed in claim 3, wherein said film further comprises lactide.

5. A method, as claimed in claim 1, wherein said step of packaging comprises enclosing said food in a material which is oxygen resistant.

6. A method, as claimed in claim 1, wherein said step of packaging comprises enclosing said food in a material which is moisture resistant.

7. A method, as claimed in claim 1, wherein said step of packaging comprises enclosing said food in a substrate selected from the group consisting of coated paper, board, polyester material, poly(vinylidine chloride) material, ethylene-vinyl alcohol copolymer material and polyolefine material.

8. A method, as claimed in claim 7, wherein said substrate is formed as a wrapping material.

9. A method, as claimed in claim 7, wherein said substrate is formed as a container.

* * * * *